United States Patent
Keeble

(10) Patent No.: US 7,254,988 B2
(45) Date of Patent: Aug. 14, 2007

(54) METHOD AND APPARATUS FOR TESTING PULSATILE ENDURANCE OF A VASCULAR IMPLANT

(75) Inventor: Duncan Robert Keeble, Didcot (GB)

(73) Assignee: Anson Medical Limited (GB)

(*) Notice: Subject to any disclaimer, the term of this patent is extended or adjusted under 35 U.S.C. 154(b) by 0 days.

(21) Appl. No.: 10/538,865

(22) PCT Filed: Dec. 16, 2003

(86) PCT No.: PCT/GB03/05467

§ 371 (c)(1),
(2), (4) Date: Nov. 18, 2005

(87) PCT Pub. No.: WO2004/054472

PCT Pub. Date: Jul. 1, 2004

(65) Prior Publication Data

US 2006/0230814 A1    Oct. 19, 2006

(30) Foreign Application Priority Data

Dec. 16, 2002 (GB) ................. 0229274.6

(51) Int. Cl.
G01N 3/36 (2006.01)
G01N 3/56 (2006.01)
A61F 2/06 (2006.01)

(52) U.S. Cl. ............ 73/37; 73/865.6; 623/912; 623/913

(58) Field of Classification Search ............ 73/1.72, 73/37, 168, 865.6, 849, 862; 623/2.11, 2.13, 623/912, 913; 435/1.2, 284.1, 286.5, 297.2, 435/399, 401; 600/36; 607/119
See application file for complete search history.

(56) References Cited

U.S. PATENT DOCUMENTS

| | | | | |
|---|---|---|---|---|
| 4,265,694 A | * | 5/1981 | Boretos et al. ............ 156/242 |
| 4,381,663 A | * | 5/1983 | Swanson ..................... 73/37 |
| 4,546,642 A | * | 10/1985 | Swanson ..................... 73/37 |
| 4,682,491 A | * | 7/1987 | Pickard ....................... 73/37 |
| 4,972,721 A | * | 11/1990 | Conti ......................... 73/807 |
| 5,327,774 A | * | 7/1994 | Nguyen et al. .............. 73/37 |
| 5,406,857 A | * | 4/1995 | Eberhardt et al. ........... 73/37 |
| 5,670,708 A | * | 9/1997 | Vilendrer .................... 73/37 |
| 5,792,603 A | | 8/1998 | Dunkelman et al. | |

(Continued)

FOREIGN PATENT DOCUMENTS

DE    199 03 476 A    8/2000

(Continued)

Primary Examiner—Hezron Williams
Assistant Examiner—David A. Rogers
(74) Attorney, Agent, or Firm—Craig A. Fieschko, Esq.; DeWitt Ross & Stevens S.C.

(57) ABSTRACT

A method for testing the pulsatile endurance of a vascular implant 3 comprises placing a resilient insert 4 into the implant and repeatedly expanding and contracting the insert, thereby expanding and contracting the implant. The insert preferably has a cavity therein and is repeatedly expanded and contracted by repeatedly increasing and decreasing the pressure in the cavity.

19 Claims, 1 Drawing Sheet

U.S. PATENT DOCUMENTS

| | | | |
|---|---|---|---|
| 6,062,075 A * | 5/2000 | Ritz et al. | 73/168 |
| 6,245,105 B1 * | 6/2001 | Nguyen et al. | 623/2.13 |
| 6,334,867 B1 | 1/2002 | Anson | |
| 6,706,064 B1 | 3/2004 | Anson | |
| 6,810,751 B2 * | 11/2004 | Moreno et al. | 73/849 |
| 6,881,224 B2 * | 4/2005 | Kruse et al. | 623/2.11 |
| 2002/0116054 A1 * | 8/2002 | Lundell et al. | 623/2.1 |
| 2003/0066338 A1 * | 4/2003 | Michalsky et al. | 73/37 |
| 2003/0110830 A1 * | 6/2003 | Dehdashtian et al. | 73/37 |

FOREIGN PATENT DOCUMENTS

| | | |
|---|---|---|
| WO | WO 00/41648 A | 7/2000 |

* cited by examiner

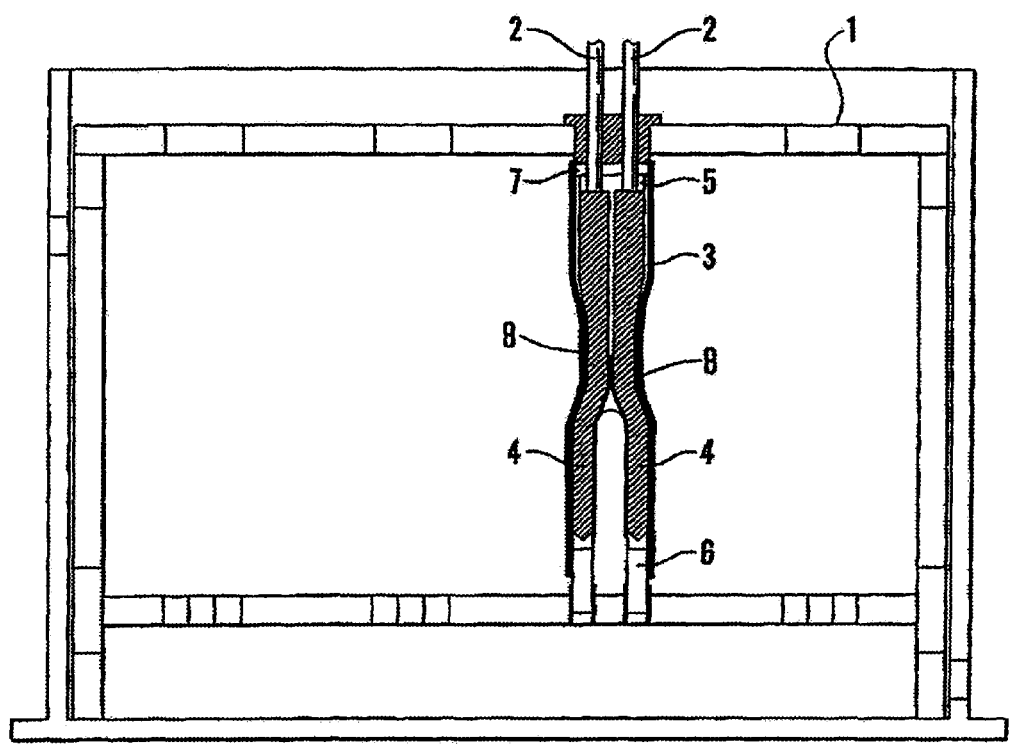

METHOD AND APPARATUS FOR TESTING PULSATILE ENDURANCE OF A VASCULAR IMPLANT

FIELD OF THE INVENTION

The present invention relates to a method and apparatus for testing pulsatile endurance of a vascular implant.

BACKGROUND OF THE INVENTION

Prosthetic vascular implants, such as heart-valves, stents, grafts and stent-grafts used for human implantation are subjected to the continuous fluctuating stress of blood pressure. It is therefore necessary to test such implants to prove their durability over a lifetime of exposure to pulsatile blood pressure.

A number of prior art documents disclose destructive methods of testing non-resilient vessels (such as glass bottles) by inserting a resilient insert such as a bladder into the vessel and subjecting the bladder to extremely high expansive pressure to see if the vessel breaks (see for example U.S. Pat. No. 3,895,514; GB 2,177,220; GB 1,531,557; and GB 2,149,126). None of these methods would be suitable for the pulsatile testing of a vascular implant.

Commercial machines for pulsatile testing of vascular implants are available from suppliers such as Enduratec Inc and Dynatek Dalta. These provide one or more resilient tubes into which the implant is placed. The tubes are filled with liquid, typically isotonic saline, and the pressure within the tube is varied by means of a pump. Different types of pump are used, some workers employ positive displacement mechanical pumps while others prefer electrically driven linear motors which drive pistons directly.

The fatigue process relies upon a first raised liquid pressure inside the tube expanding the tube and a second, lowered, liquid pressure allowing the tube to contract. As the tube expands, the radial resilience of the implant causes it to expand with the tube. As the tube contracts, it squeezes the implant back to its original size.

A similar method is disclosed in DE 199 03 476 (Inst. Implantatechnologie) which relates to a method of testing blood vessel implants by placing them inside an elastic sheath and subjecting them to external pressure.

There are a number of common failures or difficulties associated with locating the implant within a tube.

The most serious commercially is the consequence of a tube rupturing during the test. In most circumstances, a catheter or similar tube is employed to insert the implant into the tube. The implant is first crushed before passing through the catheter and this crushing process can severely affect the life expectancy of the implant. Thus, if the tube fails during a test, the tube itself can be replaced but it is not feasible to re-deliver the implant through a catheter. This is because it would involve crushing the implant into a catheter a second time and its life expectancy will consequently be reduced. The cost of replacing the implant is rarely important. However, endurance tests typically last between 3 and 6 months and such a failure can easily delay testing, and therefore the time to launch a product, by several months.

As a consequence of the above failure mode, designers of test machines will usually employ a particularly tough tube with thick walls. The compliance of such a tube (i.e. the percentage increase in diameter per unit pressure) is relatively low, and in order to achieve changes in diameter which are physiologically representative, the pulsatile pressures used to inflate the tubes are usually significantly higher than physiological pressures. For instance, in the abdominal aorta, blood pressure in the average healthy subject is 120 mm Hg/80 mm Hg, i.e. the blood pressure varies by 40 mm Hg for every pulse. Compliance of a healthy aorta can be of the order of 5% per 100 mm Hg so that a change in diameter of 2% can be expected at every heart beat. In order to simulate such a change in diameter, some workers employ a pulse pressure between 80 mm Hg and 100 mm Hg.

If the implant presents a significant surface area across the lumen of the vessel, such as a tapered stent or stent graft, then the force per unit area along the axis of the implant is increased in proportion with the inflation pressure of the tube. This elevated pressure induces failure modes such as limb separation or migration which would not occur at physiological pressures.

A shortcoming of existing designs unrelated to the failure described above lies in the limitation of the form of the tube. Stent grafts frequently are designed for use in bifurcated vessels and require bifurcated test tubes for their testing. Stent-grafts are also intended for use in aneurysms. Accordingly, where the vessel is normal, parts of the implant will be in contact with the wall of the vessel, whereas where the vessel is aneurysmal, the implant will be passing through a void. Moreover, diseased vessels are frequently highly tortuous. As a result of these factors, tubes must be available that bifurcate, that have different compliance in different places, that can be aneurysmal and which are highly tortuous. The production of such complex tubes is, even where possible, difficult, expensive and time consuming.

A further issue in endurance testing arises from the need to complete life-time tests in a commercially appropriate period of time. Typically, vascular implants are tested for 400,000,000 cycles which represent approximately 10 years of implantation life at a heart rate of 80 beats per minute. Many companies test large implants at approximately 35 Hz, allowing testing to be completed in approximately 19 weeks.

It is desirable to increase the speed of testing by as much as possible in order to accelerate the time taken to bring a new product to market. However, the testing method described above has a frequency limit which arises from the radial resilience and the surface area of the implant. This arises from the following mechanism:

When the pressure in the tube is increased, it moves away from the walls of the implant. The radial resilience of the implant causes the wall of the implant to follow the wall of the tube. However, this resilience may not be sufficient to overcome the frictional drag of the fluid through which the implant wall must move and the implant wall is likely therefore to move more slowly than the wall of the tube. Thus, where the drag is high, the radial resilience low and the testing speed is also high, the vascular implant can lag behind the movement of the wall of the tube. In these circumstances, the strain induced in the implant reduces as the frequency increases and the change in diameter of the implant no longer matches the change in diameter of the tube.

SUMMARY OF THE INVENTION

The present invention relates to an improved arrangement for testing vascular implants which overcomes or minimises all of the limitations described above.

In a first aspect of the present invention, there is provided a method for testing pulsatile endurance of a vascular implant, comprising providing a resilient insert, inserting the insert into the vascular implant, and repeatedly expanding and contracting the insert, thereby expanding and contracting the implant.

Although the insert may be such as to be expanded and contracted mechanically (for example it may comprise an expandable stent), it preferably has a cavity therein and is repeatedly expanded and contracted by repeatedly increasing and decreasing the pressure in the cavity. The preferred frequency of expansion/contraction is at least 25 Hz, more preferably from 25 to 100 Hz, most preferably from 50 to 100 Hz.

The improved technique preferably employs a tube which is deployed inside the vascular implant, the tube being made of a resilient material such as latex rubber, silicone rubber, poly-urethane or similar. Preferably, the tube is made with very thin walls so that inflation pressures within the tube are transferred directly to the inner surface of the implant under test. In practice, contraceptive condoms provide an ideal tube for testing larger implants.

Such an arrangement has the advantage that should the tube break during the test, a replacement tube can be threaded into the implant without risk of damage to the implant. In this way, failure of a tube will never automatically require the test implant to be rejected nor lose the testing time up to the moment of failure.

A second benefit of such an arrangement is that physiological pressures can be used within the tube because there is very little attenuation of the pressure by the very thin walls.

A third benefit of such a system is that the mechanical properties of the vessel surrounding the implant under test can be varied at different points and the vessel can even be made of separate components because there is no longer a requirement that the outer tube be fluid-tight. This allows the compliance of different regions to be optimised without the requirement that the entire 'vessel' is made from the same material.

A fourth benefit of the such a system is that the internal tube is very soft and this permits the test implant to be bent or angled severely, purely by means of restraints, rather than requiring a custom made, angled tube.

A fifth benefit of the system allows the test frequency to be increased because the implant is driven internally to expand rather than relying upon its radial resilience. When used in combination with an outer tube, the above described system provides a positively driven method of expanding an implant and additional resilience from the outer tube to compress an implant. The movement of the wall of the implant is then much less dependent upon the characteristics of the implant alone and testing can be carried out at frequencies of 50 Hz to 100 Hz. At this speed, testing to 400 million cycles can be completed in 7 weeks.

The diameters of implant that can be accommodated by such a machine lie in the range 2 mm to 50 mm, although if having sufficiently thin walls, the inner test tube can be significantly under- or over-sized.

The wall thickness of the inner tube preferably lies in the range from 0.03 mm to 0.2 mm, although with loss in performance, some benefits of the inner tube can still be gained if the wall thickness is several millimetres.

A preferred method of obtaining high frequency expansion and contraction of the insert is to employ a modulator such as a rotating valve or oscillating piston to modulate a continuous supply of air into a series of pulses of the required frequency.

BRIEF DESCRIPTION OF THE DRAWINGS

A preferred embodiment of the invention will now be described with reference to the drawing, in which:

FIG. 1 illustrates an arrangement of apparatus set up to test bifurcated implants in accordance with the invention.

DETAILED DESCRIPTION OF PREFERRED VERSIONS OF THE INVENTION

The apparatus of FIG. 1 comprises:
A supporting gantry (1).
Inlet tubes (2).
Vascular implant (3).
Inner tubes (4).
Short outer tube to reduce compliance at the neck of the implant (5).
Bungs (6) and (7).
Outer sheath (8).

This arrangement employs ultra-thinwalled condoms as inner tubes (4) used as apairto fill the single main body of the implant (3) and its twin legs. In order to allow higher pressures to be used within the tubes (4), bungs (6) and (7) are used to limit the extent to which each tube can expand length-wise. At each exit to the vascular implant (3), this limit is arranged to lie within a portion of outer tube which runs continuously to the vascular implant. In this way, there is no path for the inner tube to expand or herniate beyond the vascular sample or outside the outer tube. This limits the ultimate strain put on the inner tubes and prevents it from bursting unless very high pressures are employed. Additionally, to provide a compressive force to the vascular implant (3), a resilient outer sheath (8) may be provided with the vascular implant (3) being at least partially located in the outer sheath (8), wherein the vascular implant (3) presses against the outer sheath (8) during expansion.

A further improvement employed in this arrangement is the use of compressed air as the pressurising medium for the inner tubes. In order to make the air pressure pulsatile, a rotating valve or oscillating piston can be used and the design of such a valve or piston is greatly simplified by only being required to modulate the pressure of air. Other workers using saline filled systems generally require the pressure modulator to operate directly on salt water which involves the problems of corrosion and leakage.

The rotating valve (known as a "pulser") consists of a cylindrical housing into which is fitted a rotating cylinder. The cylinder has two holes through it, perpendicular to its main axis of rotation. These are perpendicular and axially displaced with respect to each other along the axis of rotation. The housing has two parallel holes through it, which are axially aligned with the holes in the cylinder.

As the cylinder rotates, the transverse holes become alternately aligned and misaligned with those in housing. When aligned with the inlet tube, pressure is transmitted to the condom. When aligned on the exhaust connection, pressure is released. Thus, as the cylinder rotates, the condom is repeatedly pressurised and depressurised. The pressure pulse may be adjusted by changing the initial air pressure, the size of the exhaust port and the speed of rotation of the cylinder.

A further benefit of employing air to pressurise the system is that the mass of oscillating fluid is significantly reduced compared to using saline solution. This in turn reduces the power required of the modulating system.

In order to employ an air pressurised system, it is still preferred that the vascular implant is maintained at physiological temperatures and in saline. Where the outer tube is discontinuous, the implant can be kept in saline by placing the entire system in a bath of salt water at an appropriate temperature.

In large implants, the change in volume per pressure pulse can be large and this places significant demands on the modulator. Compressed air systems are more demanding than liquid-filled systems in this respect because of the compressibility of the gas. In order to reduce the volume of gas in such a system, the inner tubes can be part-filled with water and small bore tubes can be used.

The invention claimed is:

1. A method for testing pulsatile endurance of a vascular implant comprising:
    a. providing a resilient insert,
    b. inserting the insert into the vascular implant,
    c. providing a resilient outer sheath, with the implant being at least partially located in the sheath, and
    d. repeatedly expanding and contracting the insert using a fluid, thereby expanding and contracting the implant, wherein the implant presses against the sheath during the implant's expansion, and the resilience of the sheath provides a compressive force to the implant.

2. The method of claim 1 wherein:
    a. the insert has a cavity therein, and
    b. the insert is repeatedly expanded and contracted by repeatedly increasing and decreasing the pressure in the cavity.

3. The method of claim 2 wherein the walls of the insert surrounding the cavity are from 0.03 to 0.2 mm thick.

4. The method of claim 2 wherein the fluid is air or a saline solution.

5. The method of claim 1 wherein the insert is a flexible tube which is closed at one end.

6. The method of claim 1 wherein the insert is formed from one of the following materials:
    a. latex rubber,
    b. silicone rubber, or
    c. polyurethane.

7. The method of claim 1 wherein the insert comprises a contraceptive condom.

8. The method of claim 1 wherein the frequency of expansion and contraction of the insert is from 50 to 100 Hz.

9. The method of claim 1 wherein the implant is at least partially immersed in saline solution during expansion and contraction.

10. The method of claim 1 wherein:
    a. the implant is a furcated graft having two or more branches extending from a juncture, and
    b. two or more of the inserts are employed, at least one insert being situated in each branch of the bifurcation.

11. The method of claim 1 wherein the implant is a vascular graft with an internal diameter from 2 to 50 mm.

12. The method of claim 1 wherein the steps of claim 1 are carried out continuously over a period of about 7 weeks.

13. The method of claim 1 wherein the contraction of the implant is due only to its inherent resilience.

14. The method of claim 1 wherein the sheath is formed of the same material as the insert.

15. A device for testing pulsatile endurance of a vascular implant comprising:
    a. a resilient insert having a cavity therein,
    b. a resilient outer sheath in which the implant is at least partially located,
    c. means for repeatedly increasing and decreasing the pressure in the cavity in order repeatedly to expand and contract the insert, thereby repeatedly expanding and contracting the implant into which, in use, the insert is inserted, wherein the sheath provides a compressive force when the implant expands against the sheath.

16. The device of claim 15 wherein the insert is flexible tube which is closed at one end.

17. The device of claim 15 wherein the means for repeatedly increasing and decreasing the pressure in the cavity can provide a frequency of expansion and contraction of the insert of from 50 to 100 Hz.

18. The device of claim 15 wherein the means for repeatedly increasing and decreasing the pressure in the cavity is a source of compressed air.

19. A device for testing pulsatile endurance of a vascular implant comprising a resilient insert having a cavity therein, and a resilient outer sheath wherein:
    a. the vascular implant is fit about the resilient insert,
    b. the resilient outer sheath is fit about the vascular implant, and
    c. the insert is repeatedly flexed by pressure variations in the cavity, wherein the insert bears against the interior of the vascular implant during flexure, and the sheath provides a compressive force when the implant expands against the sheath.

* * * * *